United States Patent
Bromidge et al.

(10) Patent No.: US 6,316,450 B1
(45) Date of Patent: Nov. 13, 2001

(54) COMPOUNDS

(75) Inventors: Steven Mark Bromidge, Harlow; Stephen Frederick Moss, Ickleton, both of (GB)

(73) Assignee: SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 09/462,652

(22) PCT Filed: Jul. 9, 1998

(86) PCT No.: PCT/EP98/04973

§ 371 Date: Jan. 10, 2000

§ 102(e) Date: Jan. 10, 2000

(87) PCT Pub. No.: WO99/02502

PCT Pub. Date: Jan. 21, 1999

(30) Foreign Application Priority Data

Jul. 11, 1997 (GB) .................................................. 9714530
Nov. 19, 1997 (GB) .................................................. 9724530

(51) Int. Cl.$^7$ .................................................. A01N 43/58
(52) U.S. Cl. ............................... 514/253.05; 514/253.06; 514/253.09; 514/255.03; 544/363; 544/373; 544/395
(58) Field of Search ........................ 514/253.05, 253.06, 514/253.09, 255.03; 544/263, 373, 395

(56) References Cited

U.S. PATENT DOCUMENTS

| 4,029,787 | 6/1977 | Sturm et al. ..................... 424/248.53 |
| 5,169,430 | * 12/1992 | Strunk ........................................ 71/92 |

FOREIGN PATENT DOCUMENTS

| 2209018 | 6/1997 | (CA) . |
| WO 95/04729 | 2/1995 | (WO) . |
| 95/16674 A1 | * 6/1995 | (WO) . |
| WO 95/15954 | 6/1995 | (WO) . |
| WO 97/07120 | 2/1997 | (WO) . |
| WO 97/14689 | 4/1997 | (WO) . |
| WO 97/29097 | 8/1997 | (WO) . |
| WO 98/27058 | 6/1998 | (WO) . |
| WO 98/27081 | 6/1998 | (WO) . |

OTHER PUBLICATIONS

Tome, Augusto C.; Cavaleiro, Jose A. S.; Domingues, Fernando M. J.; Cremlyn, Richard J., Phosphorus, Sulfur Silicon Relat. Elem., 79(1–4), 187–94 (English) 1993, cited in Chemical Abstracts, vol. 120, 1994, 134888.*

El–Kashef, Hussein S.; E–Bayoumy, Basher; Aly, Talaat I., Egypt. J. Pharm. Sci., 27(1–4), 27–35 (English) 1986.*

Tikare, R. K.; Dambal, D. B.; Pattanashetti, P. P.; Badami, B. V.; Puranik, G. S., Indian J. Chem., Sect. B, 23B(10), 1019–20 (English) 1984.*

Meneghini, Frank J. Imaging Technol., 15(3), 114–20 (English) 1989.*

F. J. Monsma, Jr., et al., "Cloning and Expression of a Novel Serotonin Receptor with High Affinity for Tricyclic Psychotrophic Drugs", (1993), Molecular Pharmacology, vol. 43:3, pp. 320–327.

D. Hoyer, et al., "5–HT Receptor Classification and Nomenclature: Towards a Harmonization with the Human Genome", (1997) Neuropharmacology, vol. 36:4/5, pp. 419–428.

F. Saudou, et al., "5–HT Receptor Subtypes: Molecular and Functional Diversity", (1994), Medicinal Chemistry Research; vol. 4:1, pp. 16–84.

R. A. Bond, et al., "Romancing Receptor Research at Verona Classification Meeting", (1996), Trends in Pharmacological Sciences; vol. 17:3, pp. 85–89.

R. M. Eglen. et al., "The 5–HT7 Receptor: Orphan Found", (1997) Trends in Pharmacological Sciences; vol. 18:4 pp. 104–107.

C. Joran–Lebrun, et al., "Arylpiperazide Derivatives of Phenylpiperazines as a New Class of Potetn and Selective 5–HT$_{1B}$ Receptor Antagonists", (1997). Bioorganic & Medicicnal Chemistry Letters; vol. 7:24, pp. 3183–3188.

G. R. Martin, et al., "The Structure and Signalling Properties of 5–HT Receptors: An Endless Diversity?", (1998) Trends in Pharmacological Sciences; vol. 19:1, pp. 2–4.

A. J. Sleight, et al., "The 5–Hydroxytryptamine$_6$ Receptor: Localisation and Function"; (1998) Exp. Opin. Ther. Patents, vol. 8:10, pp. 1217–1224.

* cited by examiner

Primary Examiner—Mukund J. Shah
Assistant Examiner—Thomas C McKenzie
(74) Attorney, Agent, or Firm—Soma G. Simon; William T. King; Charles M. Kinzig

(57) ABSTRACT

The invention relates to novel compounds having pharmacological activity, processes for their preparation, to compositions containing them and to their use in the treatment of CNS disorders.

7 Claims, No Drawings

COMPOUNDS

This invention relates to novel compounds having pharmacological activity, processes for their preparation, to compositions containing them and to their use in the treatment of CNS disorders.

EPA 0 021 580 and EPA 0 076 072 describe sulphonamide derivatives which are disclosed as having antiarrhythmic activity. A structurally distinct class of compounds has now been discovered, which have been found to have $5HT_6$ receptor antagonist activity. $5HT_6$ receptor antagonists are believed to be of potential use in the treatment of certain CNS disorders such as anxiety, depression, epilepsy, obsessive compulsive disorders, migraine, Alzheimers disease, sleep disorders (including disturbances of Circadian rhythym), feeding disorders such as anorexia and bulimia, panic attacks, withdrawal from drug abuse such as cocaine, ethanol, nicotine and benzodiazepines, schizophrenia, and also disorders associated with spinal trauma and/or head injury such as hydrocephalus. Compounds of the invention are also expected to be of utility for cognitive memory enhancement. Compounds of the invention are also expected to be of use in the treatment of certain GI (gastrointestinal) disorders such as IBS (Irritable Bowel Syndrome).

The present invention therefore provides, in a first aspect, a compound of formula (I) or a salt thereof

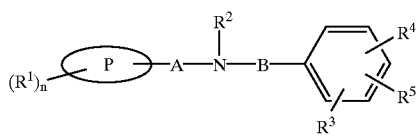

wherein:

P is phenyl, naphthyl, anthracenyl, a bicyclic heterocyclic ring, a tricyclic heteroaromatic ring or is a 5 to 7-membered heterocyclic ring each containing 1 to 4 heteroatoms selected from oxygen, nitrogen or sulphur;

A is a single bond, a $C_{1-6}$alkylene or a $C_{1-6}$alkenylene group;

B is $SO_2$;

$R^1$ is halogen, $C_{1-6}$alkyl optionally substituted by one or more fluorine atoms, $C_{3-6}$cycloalkyl, $C_{2-6}$alkenyl, $C_{1-6}$alkynyl, $C_{1-6}$alkanoyl, $C_{1-6}$alkoxy, $OCF_3$, hydroxy, hydroxy$C_{1-6}$alkyl, hydroxy$C_{1-6}$alkoxy, $C_{1-6}$alkoxy$C_{1-6}$alkoxy, nitro, cyano, $NR^{10}R^{11}$ where $R^{10}$ and $R^{11}$ are independently hydrogen, $C_{1-6}$alkyl or optionally substituted phenyl, $SR^{11}$ where $R^{11}$ is as defined above or $R^1$ is optionally substituted phenyl, naphthyl, a bicyclic heterocyclic ring, or is a 5 to 7-membered heterocyclic ring each containing 1 to 4 heteroatoms selected from oxygen, nitrogen or sulphur, or $R^1$ together with a second $R^1$ substituent forms a group —O—$CH_2$—O—, $OCH_2CH_2O$—, —$CH_2CH_2CH$— or —$CH_2CH_2CH_2CH_2$—, n is 0, 1, 2, 3, 4, 5 or 6;

$R^2$ is hydrogen, $C_{1-6}$ alkyl, aryl$C_{1-6}$ alkyl or together with group P form a 5 to 8 membered ring optionally substituted with one or more $C_{1-6}$alkyl groups;

$R^3$ is hydrogen, halogen, $C_{1-6}$alkyl, $C_{3-6}$cycloalkyl, $C_{1-6}$alkanoyl, $C_{1-6}$alkoxy optionally substituted with one or more fluorine atoms, hydroxy, hydroxy$C_{1-6}$alkyl, hydroxy$C_{1-6}$alkoxy, $C_{1-6}$alkoxy$C_{1-6}$alkoxy, nitro, trifluoromethyl, cyano or aryl or together with the group $R_5$ forms a group $(CH_2)_2O$ or $(CH_2)_3O$ optionally substituted with 1 or more $C_{1-6}$alkyl groups;

$R^4$ is —$X(CH_2)p$-$R^6$ where X is a single bond, $CH_2$, O, NH or N-alkyl and p is 0 to 6 and $R^6$ is an optionally substituted 4- to 7-membered heterocyclic ring containing 1 to 3 heteroatoms selected from nitrogen, sulphur or oxygen, or $R^6$ is $NR^7R^8$ where $R^7$ and $R^8$ are independently hydrogen, $C_{1-6}$ alkyl or aryl $C_{1-6}$ alkyl; and $R^5$ is a group $R^3$ or together with $R^3$ forms a group $(CH_2)_2O$ or $(CH_2)_3O$ optionally substituted with 1 or more $C_{1-6}$alkyl groups.

$C_{1-6}$ Alkyl groups, whether alone or as part of another group, may be straight chain or branched. As used herein the term aryl includes phenyl and naphthyl. When a group is defined as "optionally substituted", unless otherwise stated, suitable substituents include halogen, $C_{1-6}$alkyl, $C_{3-6}$cycloalkyl, $C_{1-6}$alkanoyl, $C_{1-6}$alkoxy optionally substituted with one or more fluorine atoms, hydroxy, hydroxy$C_{1-6}$alkyl, hydroxy$C_{1-6}$alkoxy, $C_{1-6}$alkoxy$C_{1-6}$alkoxy, nitro, trifluoromethyl, or cyano.

When P is a bicyclic heterocyclic ring, suitable examples include benzothiophene, indole, quinoline or isoquinoline. Bicyclic heterocyclic rings can also be partially saturated. When P is a tricyclic heteroaromatic ring suitable examples include dibenzofuran. Suitable 5 to 7-membered heterocyclic rings include thienyl, furyl, pyrrolyl, triazolyl, imidazolyl, oxazolyl, thiazolyl, oxadiazolyl, isothiazolyl, isoxazolyl, thiadiazolyl, pyridyl, pyrimidyl, pyrrolidinyl and pyrazinyl. The heterocyclic rings can be linked to the remainder of the molecule via any suitable carbon atom or, when present, a nitrogen atom. Preferably P is phenyl or naphthyl.

Suitably A is a single bond, a methylene or ethylene group or a —CH═CH-group. Preferably A is a single bond or methylene.

When $R^1$ is a a bicyclic heterocyclic ring or a 5 to 7 membered heterocyclic ring suitable examples include those listed in the definition of P.

It will be appreciated that when $R^1$ combines with a second $R^1$ substituent the two substituents must be attached to adjacent atoms on the ring P. Thus, when P is phenyl, groups such as methylenedioxyphenyl, ethylenedioxyphenyl, indane and tetrahydronapthalene are within the scope of this invention.

Suitably $R^1$ is hydrogen, halogen, phenyl, $C_{1-6}$alkoxy most preferably OMe, $SR^{11}$ most preferably SMe or $C_{1-6}$alkyl optionally substituted by one or more fluorine atoms, for example methyl or trifluoromethyl. Preferably $R^1$ is halogen. Preferably n is 0, 1, 2, 3 or 4.

Suitably $R^2$ is hydrogen, methyl or together with group P form a 5 or 6-membered ring. It will be appreciated that when groups P and $R^2$ are linked together the latter must be attached to the adjacent carbon atom on the ring P i.e. with an ortho relationship with respect to group A.

It will be appreciated that when $R^3/R^5$ groups are linked together the two groups must be attached to adjacent carbon atoms of the phenyl ring. Preferably $R^3$ is a group $R^5$, in particular hydrogen.

Preferably $R^4$ is meta with respect to the substituent B. Preferably X is a bond, p is 0 and $R^6$ is an optionally substituted 5- to 7-membered heterocyclic ring. The heterocyclic rings can be linked to the remainder of the molecule via a carbon atom or, when present, a nitrogen atom. Optional substituents for these rings, which can be present on carbon and/or nitrogen atoms, include $C_{1-6}$alkyl, in particular methyl or NR⁹R¹⁰ where $R^9$ and $R^{10}$ are independently hydrogen or $C_{1-6}$alkyl. More preferably $R^4$ is an optionally substituted piperazine. Most preferably $R^4$ is N-methyl piperazine or NH-piperazine.

Preferably $R^5$ is para with respect to the substituent B. Suitably $R^5$ is $C_{1-6}$alkoxy. Preferably $R^5$ is methoxy.

Particular compounds of the invention include:

4-Methoxy-3-(4-methylpiperazin-1-yl)-N-naphthalen-1-ylbenzenesulfonamide, N-(4-Chloronaphthalen-1-yl)-4-methoxy-3-(4-methylpiperazin-1-yl)benzene sulfonamide,
N-(3-Bromophenyl)-4-methoxy-3-(4-methylpiperazin-1-yl) benzene sulfonamide,
N-(3,4-Dichlorobenzyl)-4-methoxy-3-(4-methylpiperazin-1-yl)benzene sulfonamide,
6-Chloro-2-[4-methoxy-3-(4-methylpiperazin-1-yl)-benzenesulfonyl]-1,2,3,4-tetrahydroisoquinoline,
1-[4-Methoxy-3-(4-methyl-piperazin-1-yl)-benzene-sulfonyl]-6-trifluoromethyl-2,3-dihydro-1H-indole,
N-(3-Chlorophenyl)-4-methoxy-N-methyl-3-(4-methylpiperazin-1-yl)-benzenesulfonamide,
1-[4-Methoxy-3-(4-methylpiperazin-1-yl)-benzenesulfonyl]-7-trifluoromethyl-1,2,3,4-tetrahydroquinoline,
N-(3-Iodo-4-methylphenyl)-4-methoxy-3-(4-methylpiperazin-1-yl)-benzenesulfonamide,
N-(5-Iodo-2-methylphenyl)-4-methoxy-3-(4-methylpiperazin-1-yl)-benzenesulfonamide,
N-(3,4-Methylenedioxyphenyl)-4-methoxy-3-(4-methylpiperazin-1-yl)benzenesulfonamide,
6-Chloro-1-[4-methoxy-3-(4-methylpiperazin-1-yl) benzenesulfonyl]-5-methyl-2,3-dihydro-1H-indole,
7,8-Dichloro-2-[4-methoxy-3-(4-methylpiperazin-1-yl)-benzenesulfonyl]-1,2,3,4-tetrahydroisoquinoline,
7,8-Dimethoxy-2-[4-methoxy-3-(4-methylpiperazin-1-yl)-benzenesulfonyl]-1,2,3,4-tetrahydroisoquinoline,
5-Bromo-2-[4-methoxy-3-(4-methylpiperazin-1-yl)-benzenesulfonyl]-1,2,3,4-tetrahydroisoquinoline,
8-Chloro-7-methoxy-2-[4-methoxy-3-(4-methylpiperazin-1-yl)-benzenesulfonyl]-1,2,3,4-tetrahydroisoquinoline,
6,7-Dimethoxy-2-[4-methoxy-3-(4-methylpiperazin-1-yl)-benzenesulfonyl]-1,2,3,4-tetrahydroisoquinoline,
2-[4-methoxy-3-(4-methylpiperazin-1-yl)-benzenesulfonyl]-7-phenyl-1,2,3,4-tetrahydroisoquinoline,
8-Bromo-7-methoxy-2-[4-methoxy-3-(4-methylpiperazin-1-yl)-benzenesulfonyl]-1,2,3,4-tetrahydroisoquinoline,
5,6-Dichloro-2-[4-methoxy-3-(4-methylpiperazin-1-yl)-benzenesulfonyl]-1,2,3,4-tetrahydroisoquinoline,
5,8-Dimethoxy-2-[4-methoxy-3-(4-methylpiperazin-1-yl)-benzenesulfonyl]-1,2,3,4-tetrahydroisoquinoline,
6-Iodo-1-[4-methoxy-3-(4-methylpiperazin-1-yl) benzenesulfonyl]-5-methylthio-2,3-dihydro-1H-indole,
N-(3,4-Dichlorophenyl)-4-methoxy-3-(4-methylpiperazin-1-yl)-benzenesulfonamide,
N-(3-Iodophenyl)-4-methoxy-3-(4-methylpiperazin-1-yl)-benzenesulfonamide,
6,7,8-Trimethoxy-2-[4-methoxy-3-(4-methylpiperazin-1-yl)-benzenesulfonyl]-1,2,3,4-tetrahydroisoquinoline,
2-[4-Methoxy-3-(4-methylpiperazin-1-yl)-benzenesulfonyl]-6-pyridin-3-yl-2,3-dihydro-1H-indole,
2-[4-Methoxy-3-(4-methylpiperazin-1-yl)-benzenesulfonyl]-5-pyridin-3-yl-2,3-dihydro-1H-indole,
1-[4-Methoxy-3-(4-methylpiperazin-1-yl)-benzenesulfonyl]-1,2,3,5-tetrahydropyrrolo[2,3-f]indole,
1-(4-Methoxy-3-piperazin-1-ylbenzenesulfonyl)-7-trifluoromethyl-1,2,3,4-tetrahydroquinoline,
N-(3-Bromophenyl)-4-methoxy-3-piperazin-1-ylbenzenesulfonamide
N-(2-Fluorophenyl)-4-methoxy-3-(4-methylpiperazin-1-yl) benzenesulfonamide,
N-(2-Trifluoromethoxyphenyl)-4-methoxy-3-(4-methylpiperazin-1-yl)-benzenesulfonamide,
N-(2-Bromo-4-methylphenyl)-4-methoxy-3-(4-methylpiperazin-1-yl)-benzenesulfonamide,
N-(4-Iodophenyl)-4-methoxy-3-(4-methylpiperazin-1-yl) benzenesulfonamide,
N-(9,10-Dioxo-9,10-dihydroanthracen-1-yl)-4-methoxy-3-(4-methylpiperazin-1-yl)-benzenesulfonamide,
N-(2-Hydroxymethylphenyl)-4-methoxy-3-(4-methylpiperazin-1-yl)-benzenesulfonamide,
4-Methoxy-3-(4-methylpiperazin-1-yl)-N-(2-methylsulfanylphenyl)-benzenesulfonamide,
4-Methoxy-3-(4-methylpiperazin-1-yl)-N-(5,6,7,8-tetrahydronaphthalene-1-yl)-benzenesulfonamide,
N-(2-Ethylphenyl)-4-methoxy-3-(4-methylpiperazin-1-yl) benzenesulfonamide,
4-Methoxy-N-(2-methylphenyl)-3-(4-methylpiperazin-1-yl) benzenesulfonamide,
N-(3,4-Dimethylphenyl)-4-methoxy-3-(4-methylpiperazin-1-yl)-benzenesulfonamide,
4-Methoxy-N-(2-methoxy-6-methylphenyl)-3-(4-methylpiperazin-1-yl)-benzenesulfonamide,
N-(3-Fluoro-5-pyridin-3-ylphenyl)-4-methoxy-3-(4-methylpiperazin-1-yl)-benzenesulfonamide,
8-Chloro-2-[4-methoxy-3-(4-methylpiperazin-1-yl) benzenesulfonyl]-1,2,3,4-tetrahydroisoquinoline,
N-(2-Chloro-4-fluorophenyl)-4-methoxy-3-(4-methylpiperazin-1-yl)-benzenesulfonamide,
N-(2-Trifluoromethylphenyl)-4-methoxy-3-(4-methylpiperazin-1-yl)-benzenesulfonamide,
4-Methoxy-3-(4-methylpiperazin-1-yl)-N-quinolin-7-ylbenzenesulfonamide (E47)
N-(4-Bromophenyl)-4-methoxy-3-(4-methylpiperazin-1-yl) benzenesulfonamide,
N-(3-Bromo-4-methylphenyl)-4-methoxy-3-(4-methylpiperazin-1-yl)-benzenesulfonamide,
N-(3-Bromo-2-methylphenyl)-4-methoxy-3-(4-methylpiperazin-1-yl)-benzenesulfonamide,
4-Methoxy-N-(2-methoxydibenzofuran-3-yl)-3-(4-methylpiperazin-1-yl)-benzenesulfonamide,
N-(4-Cyclohexylphenyl)-4-methoxy-3-(4-methylpiperazin-1-yl)-benzenesulfonamide,
N-(2-Iodophenyl)-4-methoxy-3-(4-methylpiperazin-1-yl) benzenesulfonamide,
N-(2-Chloro-4-iodophenyl)-4-methoxy-3-(4-methylpiperazin-1-yl)-benzenesulfonamide,
N-(2-Bromo-4-fluorophenyl)-4-methoxy-3-(4-methylpiperazin-1-yl)-benzenesulfonamide,
N-[4-(4-Chlorophenyl)thiazol-2-yl]-4-methoxy-3-(4-methylpiperazin-1-yl)-benzenesulfonamide,
4-Methoxy-N-(3-methylphenyl)-3-(4-methylpiperazin-1-yl) benzenesulfonamide,
N-(3-Ethylphenyl)-4-methoxy-3-(4-methylpiperazin-1-yl) benzenesulfonamide,
N-(3-Chloro-4-bromophenyl)-4-methoxy-3-(4-methylpiperazin-1-yl)-benzenesulfonamide,
N-(2-Acetylphenyl)-4-methoxy-3-(4-methylpiperazin-1-yl) benzenesulfonamide,
4-Methoxy-3-(4-methylpiperazin-1-yl)-N-(4-phenylaminophenyl)-benzenesulfonamide,
4-Methoxy-3-(4-methylpiperazin-1-yl)-N-(4-pentyloxyphenyl)-benzenesulfonamide,
4-Methoxy-3-(4-methylpiperazin-1-yl)-N-(4-vinylphenyl) benzenesulfonamide, 4-Methoxy-3-(4-methylpiperazin-1-yl)-N-(2-pyrrol-1-ylphenyl)-benzenesulfonamide,
4-Methoxy-3-(4-methylpiperazin-1-yl)-N-[4-(4-nitrophenylsulfanyl)phenyl]-benzenesulfonamide,
4-Methoxy-3-(4-methylpiperazin-1-yl)-N-(3-oxazol-5-ylphenyl)-benzenesulfonamide,
N-(4-Bromo-3-trifluoromethylphenyl)-4-methoxy-3-(4-methylpiperazin-1-yl)-benzenesulfonamide,
4-Methoxy-N-(2,3-dimethylphenyl)-3-(4-methylpiperazin-1-yl)-benzenesulfonamide,
N-(4-Chloro-3-trifluoromethylphenyl)-4-methoxy-3-(4-methylpiperazin-1-yl)-benzenesulfonamide,
1-[4-Methoxy-3-(4-methylpiperazin-1-yl)benzenesulfonyl]-5-trifluoromethyl-2,3-dihydro-1H-indole,
7-Bromo-2-[4-methoxy-3-(4-methylpiperazin-1-yl)benzenesulfonyl]-1,2,3,4-tetrahydroisoquinoline,
5,8-Dichloro-2-[4-methoxy-3-(4-methylpiperazin-1-yl)benzenesulfonyl]-1,2,3,4-tetrahydroisoquinoline,
5,7-Dichloro-1-[4-methoxy-3-(4-methylpiperazin-1-yl)benzenesulfonyl]-1,2,3,4-tetrahydroquinoline,
1-[4-Methoxy-3-(4-methylpiperazin-1-yl)benzenesulfonyl]-1,2,3,4-tetrahydroquinoline,
1-[4-Methoxy-3-(4-methylpiperazin-1-yl)benzenesulfonyl]-6-methyl-1,2,3,4-tetrahydroquinoline,
6-Fluoro-1-[4-methoxy-3-(4-methylpiperazin-1-yl)benzenesulfonyl]-1,2,3,4-tetrahydroquinoline,
5-Chloro-2-[4-methoxy-3-(4-methylpiperazin-1-yl)-benzenesulfonyl]-2,3-dihydro-1H-isoindole hydrochloride,
N-(2-Isopropylphenyl)-4-methoxy-3-piperazin-1-yl-benzenesulfonamide hydrochloride,
N-(4-Chloronaphthalen-1-yl)-4-methoxy-3-piperazin-1-ylbenzenesulfonamide,
4-Methoxy-N-naphthalen-1-yl-3-piperazin-1-ylbenzenesulfonamide,
N-(3-Chloro-2-methylphenyl)-4-methoxy-3-piperazin-1-ylbenzenesulfonamide,
N-Indan-5-yl-4-methoxy-3-piperazin-1-ylbenzenesulfonamide,
N-(2-Fluorophenyl)-4-methoxy-3-piperazin-1-ylbenzenesulfonamide,
4-Methoxy-N-(2-methylsulfanylphenyl)-3-piperazin-1-ylbenzenesulfonamide,
4-Methoxy-3-piperazin-1-yl-N-(2-trifluoromethylphenyl)benzenesulfonamide,
4-Methoxy-N-(2-methylphenyl)-3-piperazin-1-ylbenzenesulfonamide,
N-(2-Ethylphenyl)-4-methoxy-3-piperazin-1-ylbenzenesulfonamide,
4-Methoxy-3-piperazin-1-yl-N-(3-trifluoromethylphenyl)benzenesulfonamide,
N-(3,4-Dimethylphenyl)-4-methoxy-3-piperazin-1-ylbenzenesulfonamide,
N-(2-Bromophenyl)-4-methoxy-3-piperazin-1-ylbenzenesulfonamide,
N-(3,4-Dichlorophenyl)-4-methoxy-3-piperazin-1-ylbenzenesulfonamide,
N-(3-Iodophenyl)-4-methoxy-3-piperazin-1-ylbenzenesulfonamide,
N-(3,5-Dichlorophenyl)-4-methoxy-3-piperazin-1-ylbenzenesulfonamide,
N-(3-Chlorophenyl)-4-methoxy-3-piperazin-1-ylbenzenesulfonamide,
N-(2-Chloro-3-fluoro-4-methylphenyl)-4-methoxy-3-piperazin-1-yl-benzenesulfonamide,
N-(4-Chloro-3-methylphenyl)-4-methoxy-3-piperazin-1-ylbenzenesulfonamide,
N-Benzo[1,3]dioxol-5-yl-4-methoxy-3-piperazin-1-ylbenzenesulfonamide,
N-(2-Bromo-4-methylphenyl)-4-methoxy-3-piperazin-1-ylbenzenesulfonamide,
N-(2,5-Dibromophenyl)-4-methoxy-3-piperazin-1-ylbenzenesulfonamide,
N-(2,5-Dichlorophenyl)-4-methoxy-3-piperazin-1-ylbenzenesulfonamide,
N-(2-Chloro-4-methylphenyl)-4-methoxy-3-piperazin-1-ylbenzenesulfonamide,
N-(4-Bromophenyl)-4-methoxy-3-piperazin-1-ylbenzenesulfonamide,
N-(2-Isopropenylphenyl)-4-methoxy-3-piperazin-1-ylbenzenesulfonamide,
4-Methoxy-N-(2-methyl-5-nitrophenyl)-3-piperazin-1-ylbenzenesulfonamide,
N-(4-Iodophenyl)-4-methoxy-3-piperazin-1-ylbenzenesulfonamide,
N-(4-tert-Butylphenyl)-4-methoxy-3-piperazin-1-ylbenzenesulfonamide,
N-(4-Isopropylphenyl)-4-methoxy-3-piperazin-1-ylbenzenesulfonamide,
N-(4-Hexylphenyl)-4-methoxy-3-piperazin-1-ylbenzenesulfonamide,
N-(2,4-Dibromonaphthalen-1-yl)-4-methoxy-3-piperazin-1-ylbenzenesulfonamide,
4-Methoxy-N-(4-methoxybiphenyl-3-yl)-3-piperazin-1-ylbenzenesulfonamide,
N-(3-Fluoro-5-pyridin-3-ylphenyl)-4-methoxy-3-piperazin-1-yl-benzenesulfonamide,
N-Biphenyl-2-yl-4-methoxy-3-piperazin-1-ylbenzenesulfonamide,
N-(2-Benzylphenyl)-4-methoxy-3-piperazin-1-ylbenzenesulfonamide,
N-(2-Propylphenyl)-4-methoxy-3-piperazin-1-ylbenzenesulfonamide,
N-(2-sec-Butylphenyl)-4-methoxy-3-piperazin-1-ylbenzenesulfonamide,
N-(2-tert-Butylphenyl)-4-methoxy-3-piperazin-1-ylbenzenesulfonamide,
N-(2-Butylphenyl)-4-methoxy-3-piperazin-1-ylbenzenesulfonamide,
N-(5-Iodo-2-methylphenyl)-4-methoxy-3-piperazin-1-yl-benzenesulfonamide,
6-Chloro-1-(4-methoxy-3-piperazin-1-ylbenzenesulfonyl)-5-methyl-2,3-dihydro-1H-indole hydrochloride,
6-Iodo-1-(4-methoxy-3-piperazin-1-ylbenzenesulfonyl)-5-methylsulfanyl-2,3-dihydro-1H-indole,
6-Bromo-1-(4-methoxy-3-piperazin-1-ylbenzenesulfonyl)-1,2,3,4-tetrahydroquinoline,
8-Chloro-2-(4-methoxy-3-piperazin-1-ylbenzenesulfonyl)-1,2,3,4-tetrahydroisoquinoline,
1-(4-Methoxy-3-piperazin-1-ylbenzenesulfonyl)-5-methyl-6-trifluoromethyl-2,3-dihydro-1H-indole,
5,8-Dimethoxy-2-(4-methoxy-3-piperazin-1-ylbenzensulfonyl)-1,2,3,4-tetrahydroisoquinoline hydrochloride,
5,8-Dichloro-2-(4-methoxy-3-piperazin-1-ylbenzenesulfonyl)-1,2,3,4-tetrahydroisoquinoline hydrochloride,
N-(3-Iodo-4-methylphenyl)-4-methoxy-3-piperazin-1-yl-benzenesulfonamide,
5,7-Dichloro-1-(4-methoxy-3-piperazin-1-ylbenzenesulfonyl)-1,2,3,4-tetrahydroquinoline,
N-(2-Chloro-3,5-difluorophenyl)-4-methoxy-3-piperazin-1-ylbenzenesulfonamide,
N-(4-Chloro-2-trifluoromethoxyphenyl)-4-methoxy-3-piperazin-1-ylbenzenesulfonamide, N-(2,4,5-Trichlorophenyl)-4-methoxy-3-piperazin-1-ylbenzenesulfonamide,
N-(5-Chloro-2-methoxyphenyl)-4-methoxy-3-piperazin-1-ylbenzenesulfonamide,
N-(4-Chloro-2-trifluoromethylphenyl)-4-methoxy-3-piperazin-1-ylbenzenesulfonamide,
N-(3,5-Dibromophenyl)-4-methoxy-3-piperazin-1-ylbenzenesulfonamide,
N-(3-Bromo-2,5-dichlorophenyl)-4-methoxy-3-piperazin-1-ylbenzenesulfonamide,
N-(2,3,5-Trichlorophenyl)-4-methoxy-3-piperazin-1-ylbenzenesulfonamide,
N-(5-Bromo-2,3-dihydro-benzofuran-7-yl)-4-methoxy-3-piperazin-1-ylbenzenesulfonamide,
N-(2-Bromo-3,5-dichlorophenyl)-4-methoxy-3-piperazin-1-ylbenzenesulfonamide,
N-(3-Bromo-5,6-dichlorophenyl)-4-methoxy-3-piperazin-1-ylbenzenesulfonamide,
N-(2,5-Dibromo-3-fluorophenyl)-4-methoxy-3-piperazin-1-ylbenzenesulfonamide
N-(2,5-Dibromo-3-chlorophenyl)-4-methoxy-3-piperazin-1-ylbenzenesulfonamide
N-(2,3,5-Tribromophenyl)-4-methoxy-3-piperazin-1-ylbenzenesulfonamide
6-Iodo-1-(4-methoxy-3-piperazin-1-ylbenzenesulfonyl)-2,3-dihydro-1H-indole,
5-Iodo-1-(4-methoxy-3-piperazin-1-ylbenzenesulfonyl)-2,3-dihydro-1H-indole,
7-Bromo-1-(4-methoxy-3-piperazin-1-ylbenzenesulfonyl)-1,2,3,4-tetrahydroquinoline and pharmaceutically acceptable salts thereof.

The compounds of the formula (I) can form acid addition salts with acids, such as conventional pharmaceutically acceptable acids, for example maleic, hydrochloric, hydrobromic, phosphoric, acetic, fumaric, salicylic, citric, lactic, mandelic, tartaric and methanesulphonic.

Compounds of formula (I) may also form solvates such as hydrates, and the invention also extends to these forms. When referred to herein, it is understood that the term 'compound of formula (I)' also includes these forms.

Certain compounds of formula (I) are capable of existing, in stereoisomeric forms including diastereomers and enantiomers and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

The present invention also provides a process for the preparation of a compound of formula (I) or a pharmaceutically acceptable salt thereof, which process comprises the coupling of a compound of formula (II):

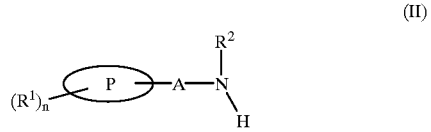

(II)

in which $R^1$, $R^2$, n, P, and A are as defined in formula (I) or protected derivatives thereof with a compound of formula (III):

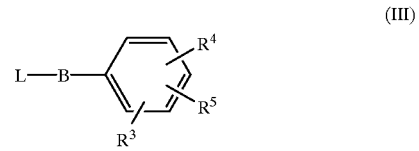

(III)

in which B, $R^3$, $R^4$ and $R^5$ are as defined in formula (I) or protected derivatives thereof and L is a leaving, group and optionally thereafter:
removing any protecting groups,
forming a pharmaceutically acceptable salt.

Suitable leaving groups include halogen, in particular chloro. The reaction of a compounds of formulae (II) and (III) is carried out by mixing the two reagents together, optionally in an inert solvent such as dichloromethane with or without the addition of a suitable base such as triethylamine [or pyridine].

Those skilled in the art will appreciate that it may be necessary to protect certain groups. Suitable protecting groups and methods for their attachment and removal are conventional in the art of organic chemistry, such as those described in Greene T. W. 'Protective groups in organic synthesis' New York, Wiley (1981).

Compounds of formulae (II) and (III) are commercially available or may be prepared according to known methods or analogous to known methods. For example to prepare compounds of formulae (I) where $R^3$ is H, $R^5$ is OMe and $R^4$ is 1-piperazine a suitable protecting group in intermediates of formulae (III) was found to be trichloroacetyl. Thus reacting 1-(2-methoxyphenyl) piperazine with trichloroacetyl chloride in a suitable solvent such as dichloromethane in the presence of a base such as diisopropylethylamine afforded 2-(4-trichloroacetyl-piperazin-1-yl) anisole. On treatment with chlorosulfonic acid at 0° C. in a suitable inert solvent such as dichloromethane 3-(4-trichloroacetylpiperazin-1-yl)-4-methoxybenzenesulfonyl chloride was obtained. Coupling of this compound with compounds of formulae (II) as described above followed by treatment with 20% aqueous potassium hydroxide afforded the required compound.

Pharmaceutically acceptable salts may be prepared conventionally by reaction with the appropriate acid or acid derivative.

Compounds of formula (I) and their pharmaceutically acceptable salts have $5HT_6$ receptor antagonist activity and are believed to be of potential use in the treatment of certain CNS disorders such as anxiety, depression, epilepsy, obsessive compulsive disorders, migraine, Alzheimers disease, sleep disorders (including disturbances of Circadian rhythym), feeding disorders such as anorexia and bulimia, panic attacks, withdrawal from drug abuse such as cocaine, ethanol, nicotine and benzodiazepines, schizophrenia, and also disorders associated with spinal trauma and/or head injury such as hydrocephalus. Compounds of the invention are also expected to be of use in the treatment of certain GI disorders such as IBS.

Thus the invention also provides a compound of formula (I) or a pharmaceutically acceptable salt thereof, for use as a therapeutic substance, in particular in the treatment or prophylaxis of the above disorders.

The invention further provides a method of treatment or prophylaxis of the above disorders, in mammals including humans, which comprises administering to the sufferer a therapeutically effective amount of a compound of formula (I) or a pharmaceutically acceptable salt thereof.

In another aspect, the invention provides the use of a compound of formula (I) or a pharmaceutically acceptable salt thereof in the manufacture of a medicament for the treatment or prophylaxis of the above disorders.

The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusable solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 0.05 to 20.0 mg, for example 0.2 to 5 mg; and such unit doses may be administered more than once a day, for example two or three a day, so that the total daily dosage is in the range of about 0.5 to 100 mg; and such therapy may extend for a number of weeks or months.

When administered in accordance with the invention, no unacceptable toxicological effects are expected with the compounds of the invention.

The following Descriptions and Examples illustrate the preparation of compounds of the invention.

Description 1

2-(4-Methylpiperazin-1-yl)anisole (D1)

To an ice-cooled, stirred suspension of lithium aluminium hydride (7.9 g, 0.21 mol) in dry tetrahydrofuran (1 50 ml) was added a solution of 1-(2-methoxyphenyl) piperazine (10 g, 52 mmol) in dry tetrahydrofuran (150 ml) over 0.5 h under argon. A solution of ethyl formate (12.6 ml, 0.156 mol) in dry tetrahydrofuran (25 ml) was added to the cold mixture over 0.25 h and the resulting suspension was stirred for a further 2 h at room temperature. Dilute sodium hydroxide solution (15%, 8 ml) was slowly added to the cooled mixture, followed by water (24 ml) and the whole left to stir for 0.25 h. The mixture was filtered and the filtrate concentrated to an oil which was partitioned between dichloromethane and water. The organic phase was dried and concentrated to an oil which was purified by column chromatography on silica gel eluting with a methanol/dichloromethane gradient to afford the title compound as a colourless oil (5.7 g, 53%)

$\delta_H$ (250 MHz, CDCl$_3$), 2.36 (3H, s), 2.63 (4H, br s), 3.10 (4H, br s), 3.86 (3H, s), 6.84–7.03 (4H, m).

Description 2

3-(4-Methylpiperazin-1-yl)-4-methoxybenzene sulfonyl chloride (D2)

2-(4-Methylpiperazin-1-yl)anisole (200 mg, 1 mmol) was added in portions over ten minutes to ice-cooled, stirred chlorosulfonic acid (1.2 ml) under argon. The resulting brown solution was stirred at 0° C. for 0.25 h and then at ambient temperature for a further 1.25 h. The solution was slowly poured onto crushed ice (50 g). Dichloromethane (50 ml) was added to the mixture followed by saturated sodium carbonate solution until pH10 was attained in the aqueous phase. The layers were separated and the aqueous phase further extracted with dicholoromethane. The combined organic phases were dried (Na$_2$SO$_4$) and concentrated to an oil. The oil was stirred with hexane (4 ml) to give the title compound as a cream solid (210 mg, 71%).

$\delta_H$ (250 MHz, CDCl$_3$) 2.43 (3H, s), 2.71 (4H, br t, J=4.2), 3.20 (4H, br t, J=4.2), 4.00 (3H, s), 6.97 (1H, d, J8.7), 7.48 (1H, d, J2.2), 7.72 (1H, dd, J2.2, 8.7), MS: m/z (MH$^+$)=305.

Description 3

2-(4-Trichloroacetylpiperazin-1-yl) anisole (D3)

A solution of 1-(2-methoxyphenyl) piperazine (7.0 g) in dichloromethane (30 ml) was added over 0.25 h to a stirred solution of trichloroacetyl chloride (4.06 ml) in dichloromethane (40 ml) at room temperature under argon. Diisopropylethylamine (5.95 ml) was then added and the whole was stirred for 18 h. The reaction mixture was washed with water (2×100 ml), dried (Na$_2$SO$_4$) and concentrated to give the title compound (D3) as an oil (11.2 g, 91%). MH$^+$337/339.

Description 4

3-(4-Trichloroacetylpiperazin-1-yl)-4-methoxybenzenesulfonyl chloride (D4)

A solution of 2-(4-trichloroacetylpiperazin-1-yl) anisole (D3) (10 g) in dichloromethane (115 ml) was added over 0.3 h to ice-cooled chlorosulfonic acid (52 ml). After 0.5 h at 0° C. then 1 h at ambient temperature, the solution was poured onto a mixture of ice-water (500 g) and dichloromethane (500 ml) with rapid stirring. The layers were separated and the organic phase was washed with water (2×800 ml), dried (MgSO$_4$) and concentrated to give the title compound (D4) as a foam (6.0 g, 46%). MH$^+$ 435/437.

Description 5

6-Iodo-2,3-dihydro-1H-indole (D5)

This compound was prepared as previously described (Heterocycles, 1987, 26, 2817)

Description 6

5-Iodo-2,3-dihydro-1H-indole (D6)

This compound was prepared as previously described (Chem. Pharm. Bull. 1987, 35, 3146.)

Description 7

3,5-Dibromoaniline (D7)

A suspension of 3,5-dibromo nitrobenzene (J. Amer. Chem Soc., 1950, 72, 793) (1.0 g, 3.6 mmol) in methanol (30 ml) was added in portions to a stirred mixture of iron powder (0.52 g, 9.3 mmol) in a saturated solution of ammonium chloride (50 ml) at 60° C. The mixture was heated at reflux for 2 h, filtered and the filtrate extracted with dichloromethane (2×70 ml). The organic extract was dried (Na$_2$SO$_4$) and concentrated in vacuo to give the title compound (D7) as an oil (0.787 g, 87%), MH$^+$ 250/252.

Description 8

2-Bromo-3,5-dichloro-4-nitroaniline (D8)

A solution of N-bromosuccinimide (2.6 g, 14.5 mmol) in N,N-dimethylformamide (DMF) (70 ml) was added over 20 min to a stirred solution of 2,5-dichloro-4-nitroaniline (3.0 g, 14.5 mmol) in DMF (30 ml) at room temperature under argon. After stirring for 18 h, the mixture was poured into water (11) and extracted with dichloromethane (500 ml). The organic extract was washed with water (5×500 ml), dried (MgSO$_4$) and concentrated to an oil which was purified by column chromatography over silica gel eluting with ethyl acetate/hexane gradient to give the title compound (D8) as a yellow solid (1.0 g, 24%), MH$^+$ 285/287.

Description 9

3-Bromo-2,5-dichloro nitrobenzene (D9)

Concentrated sulphuric acid (2.2 ml) was slowly added to a suspension of 2-bromo-3,5-dichloro-4-nitroaniline (D8) (0.9 g, 3.1 mmol) in ethanol (20 ml). The resulting solution was heated to reflux and crushed sodium nitrite (478 mg, 6.9 mmol) was added in two portions. After 0.5 h at reflux, the mixture was cooled, diluted with dichloromethane (50 ml) and saturated sodium hydrogen carbonate solution (50 ml) was added. The layers were separated and the organic phase dried (Na$_2$SO$_4$) and concentrated to an oil which was purified by column chromatography over silica gel eluting with a gradient of ethyl acetate/hexane to give the title compound (D9) as an orange solid (0.67 g, 80%), MH$^+$ 269/271.

Description 10

3-Bromo-2,5-dichloroaniline (D10)

3-Bromo-2,5-dichloro nitrobenzene (D9) was treated with iron powder in the manner described in Description 7 to give the title compound (D10) as a solid (77%), MH$^+$ 240/242.

Description 11

2,3,6-trichloro-4-nitroaniline (D11)

To a suspension of 2,5-dichloro-4-nitroaniline (4.0 g, 19.3 mmol) in ethanol (50 ml) was added concentrated hydrochloric acid (20 ml) and water (20 ml). The mixture was heated to 50° C. and 27.5% hydrogen peroxide (6 ml) added over 15 min. The mixture was maintained at this temperature for a further 2 h, cooled to room temperature, and the solid filtered and washed with water (2×20 ml) to give the title compound (D11) (4.1 g, 88%), MH$^+$ 241/243.

Description 12

2,3,5-Trichloro nitrobenzene (D12)

2,3,6-Trichloro-4-nitroaniline (D11) was deaminated as described in Description 9 to give the title compound (D12) (64%), MH$^+$ 226/228.

Description 13

2,3,5-Trichloroaniline (D13)

2,3,5-Trichloro nitrobenzene (D12) was reduced with iron powder as described in Description 7 to give the title compound (D13) (68%), MH$^+$ 196/198.

Description 14

7-Amino-5-bromo-2,3-dihydrobenzofuran (D14)

Concentrated sulfuric acid (8.8 ml) was added over 5 min to a stirred mixture of 5-bromo-2,3-dihydrobenzofuran-7-carboxylic acid (0.55 g, 2.3 mmol) in chloroform (27 ml) at 45° C. Sodium azide (0.737 g, 11.3 mmol) was then added portion-wise over 0.5 h and the temperature was maintained for a further 1 h after which time the mixture was poured onto ice (100 g) and extracted with chloroform (2×50 ml). The aqueous phase was basified to pH 12 with 40% sodium hydroxide solution and extracted with chloroform (2×50 ml). The extract was dried (Na$_2$SO$_4$), concentrated, and the residue purified by column chromatography over silica gel eluting with a gradient of acetone/toluene to give the title compound (D14) as a solid (63 mg, 13%), MH$^+$ 214/216.

Description 15

7-Bromo-1,2,3,4-tetrahydroquinoline (D15)

A solution of 7-bromoquinoline (J. Amer. Chem. Soc., 1947, 69, 705) (362 mg, 1.74 mmol) in glacial acetic acid (10 ml) was treated portion-wise with sodium cyanoborohydride (437 mg, 7.0 mmol) under argon at room temperature. After 18 h at this temperature, the mixture was cooled in an ice bath and to it was added water (35 ml) and 50% aq. sodium hydroxide until pH 14 was attained. The mixture was extracted with dichloromethane and the organic phase washed with saturated sodium chloride solution, dried (Na$_2$SO$_4$) and concentrated in vacuo to a residue which was purified by column chromatography over silica gel eluting with a gradient of methanol/dichloromethane to give the title compound (D15) (168 mg, 46%). MH$^+$ 212/214.

Description 16

3-(4-Methyl-1-piperazin-1-yl)-4-methoxybenzenesulphonamide (D16)

The title compound (D16) was prepared in 35% yield by treating the sulfonyl chloride (D2) with excess aqueous ammonia in acetone.

Many of the intermediates used in the preparation of the compounds of this invention can be prepared by known procedures. These are shown in Table A.

TABLE A

| Description No. | Compound Name | Reference |
| --- | --- | --- |
| Description 17 | 6-Trifluoromethyl-2,3-dihydro-1H-indole (D17) | J. Med. Chem. 1998, 41(10), 1598–1612 |
| Description 18 | 6-Chloro-5-methyl-2,3-dihydro-1H-indole (D18) | WO-95/01976 |
| Description 19 | 7,8-Dichloro-1,2,3,4-tetrahydroisoquinoline (D19) | J. Org. Chem. 1980, 45(10), 1950–3 |
| Description 20 | 7,8-Dimethoxy-1,2,3,4-tetrahydroisoquinoline (D20) | J. Org. Chem. 1968, 33(2), 494–503 |
| Description 21 | 5-Bromo-1,2,3,4-tetrahydroisoquinoline (D21) | WO-95/13274 |
| Description 22 | 8-Chloro-7-methoxy-1,2,3,4-tetrahydroisoquinoline (D22) | J. Med. Chem. 1982, 25(10), 1235–40 |
| Description 23 | 6,7-Dimethoxy-1,2,3,4-tetrahydroisoquinoline (D23) | J. Org. Chem. 1968, 33(2), 494–503 |
| Description 24 | 7-phenyl-1,2,3,4-tetrahydroisoquinoline (D24) | J. Pharm. Sci. 1970, 59(1), 59–62 |
| Description 25 | 8-Bromo-7-methoxy-1,2,3,4-tetrahydroisoquinoline (D25) | J. Het. Chem. 1978, 15(3), 429–32 |
| Description 26 | 5,6-Dichloro-1,2,3,4-tetrahydroisoquinoline (D26) | J. Med. Chem. 1980, 25(3), 506–11 |
| Description 27 | 5,8-Dimethyl-1,2,3,4-tetrahydroisoquinoline (D27) | J. Med. Chem. 1981, 24(12), 1432–7 |
| Description 28 | 6-Iodo-5-methylthio-2,3-dihydro-1H-indole (D28) | WO-95/01976 |
| Description 29 | 6,7,8-Trimethoxy-1,2,3,4-tetrahydroisoquinoline (D29) | Heterocycles 1989, 29(6), 2817–22 |
| Description 30 | 6-pyridin-3-yl-2,3-dihydro-1H-indole (D30) | FR-2530246 CA:101:23351 |
| Description 31 | 5-pyridin-3-yl-2,3-dihydro-1H-indole (D31) | FR-2530246 CA:101:23351 |
| Description 32 | 1,2,3,5-tetrahydropyrrolo-[2,3-f]indole (D32) | J. Med. Chem. 1996, 39(25), 4966–77 |
| Description 33 | 3-Fluoro-5-pyridin-3-ylaniline (D33) | WO-96/23783 |
| Description 34 | 8-Chloro-1,2,3,4-tetrahydroisoquinoline (D34) | J. Med. Chem. 1980, 23(5), 506–11 |
| Description 35 | 5-Trifluoromethyl-2,3-dihydro-1H-indole (D35) | WO-97/48700 |
| Description 36 | 7-Bromo-1,2,3,4-tetrahydroisoquinoline (D36) | WO-98/06699 |
| Description 37 | 5,8-Dichloro-1,2,3,4-tetrahydroisoquinoline (D37) | J. Med. Chem. 1980, 23(5), 506–11 |
| Description 38 | 5,7-Dichloro-1,2,3,4-tetrahydroquinoline (D38) | J. Med. Chem. 1980, 23(5), 506–11 |
| Description 39 | 6-Fluoro-1,2,3,4-tetrahydroquinoline (D39) | JP-55040616 |
| Description 40 | 6-Bromo-1,2,3,4-tetrahydroquinoline (D40) | EP-702004 |
| Description 41 | 8-Chloro-1,2,3,4-tetrahydroisoquinoline (D41) | J. Med. Chem. 1980, 23(5), 506–11 |
| Description 42 | 5-Methyl-6-trifluoromethyl-2,3-dihydro-1H-indole (D42) | WO-97/48700 |
| Description 43 | 5,7-Dichloro-1,2,3,4-tetrahydroquinoline (D43) | JP-55040616 |

EXAMPLE 1

4-Methoxy-3-(4-methylpiperazin-1-yl)-N-naphthalen-1-ylbenzenesulfonamide hydrochloride (E1)

1-Naphthylamine (29 mg, 0.2 mmol) was added to a stirred solution of 3-(4-methyl-1-piperazinyl)-4-methoxybenzene sulfonyl chloride (D2) (60 mg, 0.2 mmol) in acetone (1 ml) at ambient temperature. After stirring, for 18 h, the precipitate was filtered off and washed with acetone and diethyl ether to afford the title compound (E1) as a cream solid (60 mg, 67%).

$\delta_H$ (250 MHz, DMSO-d$_6$) 2.88 (3H,s), 2.90–2.97 (2H, m), 3.15–3.30 (2H, m), 3.37–3.56 (4H, m), 3.89 (3H, s), 7.11 (1H, d J=8.8), 7.22–7.59 (6H, m), 7.86 (1H, d, J=8.3), 7.96 (1H, d, J=9.0), 8.10 (1H, d, J=7.0), 10.18 (1H, s), 10.55 (1H, br s). MS: m/z (MH$^+$–HCl)=412.

The compounds in Tables 1 and 2 were prepared in a similar manner to Example 1 using 3-(4-methylpiperazin-1-yl)-4-methoxybenzene sulfonyl chloride (D2) and the appropriate amine. All amines are either commercially available or can be prepared by methods as referenced in Table A above. If required purification by recrystalisation or alternatively by aqueous basic (K$_2$CO$_3$) workup followed by column chromatography was carried out.

TABLE 1

| Compound | $\delta_H$(250 MHz, DMSO-d6) | MS (MH$^+$) |
| --- | --- | --- |
| N-(4-Chloronaphthalen-1-yl)-4-methoxy-3-(4-methylpiperazin-1-yl)benzene sulfonamide hydrochloride (E2) | 2.75(3H, d, J=4.5), 2.70–2.84(2H, m), 3.02–3.15(2H, m), 3.25–3.45(4H, m), 3.74(3H, s), 6.95(1H, d, J=8.5), 7.07–7.13(2H, m), 7.21(1H, d, J=8.5), 7.48–7.62(3H, m), 8.04(1H, t, J=7.2), 10.11(1H, s), 10.20(1H, br s). | 446 |
| N-(3-Bromophenyl)-4-methoxy-3-(4-methylpiperazin-1- | 2.68(3H, d J3.5), 2.78–2.88(2H, br m), 3.0–3.10(2H, m), 3.30–3.40(4H, | 440 |

TABLE 1-continued

| Compound | δ$_H$(250 MHz, DMSO-d6) | MS (MH$^+$) |
|---|---|---|
| yl)benzene sulfonamide hydrochloride (E3) | m), 3.71(3H, s), 6.96–7.32(7H, m), 10.31(1H, s), 10.47(1H, br s). | |
| N-(3,4-Dichlorobenzyl)-4-methoxy-3-(4-methylpiperazin-1-yl)benzene sulfonamide hydrochloride (E4) | 2.80(3H, s), 3.06–3.55(8H, m), 3.86 (3H, s), 4.00(2H, d J=6.4), 7.06 (1H, d, J=8.6), 7.18–7.22(2H, m), 7.35–7.40(2H, m), 7.50(1H, d, J=8.3), 8.18(1H, s), 10.83(1H, s). | 444 |
| 6-Chloro-2-[4-methoxy-3-(4-methylpiperazin-1-yl)-benzenesulfonyl]-1,2,3,4-tetrahydroisoquinoline hydrochloride (E5) | 2.68(3H, s), 2.89–3.31 (12H, m), 3.74 (3H, s), 4.12(2H, t, J=16.5), 7.01–7.11(6H, m), 7.38–7.48(2H, m), 9.15 (1H, s), 10.91(1H, s). | 436 |
| 1-[4-Methoxy-3-(4-methyl-piperazin-1-yl)-benzene-sulfonyl]-6-trifluoromethyl-2,3-dihydro-1H-indole hydrochloride (E6) | 2.64(3H, s), 2.80–3.03(6H, m), 3.20–3.39(4H, m), 3.68(3H, s), 3.74–3.81 (2H, t, J=8.6), 6.95(1H, d, J=2.2), 7.02–7.07(1H, d, J=13.0), 7.21–7.22 (2H, d, J=2.1), 7.30–7.35(1H, dd, J=2.2, 8.6), 7.50(1H, s), 10.65(1H, s). | 456 |
| N-(3-Chlorophenyl)-4-methoxy-N-methyl-3-(4-methylpiperazin-1-yl)-benzenesulfonamide (E7) | 2.34(3H, s), 2.57(4H, s), 2.97(4H, s), 3.10(3H, s), 393(3H, s), 6.87–6.90(2H, m), 7.04–7.10(2H, m), 7.18–7.31(2H,m). | 410 |
| 1-[4-Methoxy-3-(4-methylpiperazin-1-yl)-benzenesulfonyl]-7-trifluoromethyl-1,2,3,4-tetrahydroquinoline (E8) | 1.59–1.69(2H, m), 2.33(3H, s), 2.41–2.52(6H, br s), 2.90(4H, s), 380(2H, t, J5.7), 3.89(3H, s), 6.83(1H, d, J=8.6), 6.94(1H, d J=2.2), 7.06–7.10 (1H, d, J=7.9), 7.29(1H, s), 7.35(1H, dd, J=2.3, 8.5), 816(1H, s). | 470 |

TABLE 2

| Compound | MS (MH$^+$) |
|---|---|
| N-(3-Iodo-4-methylphenyl)-4-methoxy-3-(4-methylpiperazin-1-yl)-benzenesulfonamide hydrochloride (E9) | 502 |
| N-(5-Iodo-2-methylphenyl)-4-methoxy-3-(4-methylpiperazin-1-yl)-benzenesulfonamide hydrochloride (E10) | 502 |
| N-(3,4-Methylenedioxyphenyl)-4-methoxy-3-(4-methylpiperazin-1-yl)benzenesulfonamide hydrochloride (E11) | 406 |
| 6-Chloro-1-[4-methoxy-3-(4-methylpiperazin-1-yl)benzenesulfonyl]-5-methyl-2,3-dihydro-1H-indole (E12) | 436 |
| 7,8-Dichloro-2-[4-methoxy-3-(4-methylpiperazin-1-yl)-benzenesulfonyl]-1,2,3,4-tetrahydroisoquinoline hydrochloride (E13) | 470/472 |
| 7,8-Dimethoxy-2-[4-methoxy-3-(4-methylpiperazin-1-yl)-benzenesulfonyl]-1,2,3,4-tetrahydroisoquinoline hydrochloride (E14) | 462 |
| 5-Bromo-2-[4-methoxy-3-(4-methylpiperazin-1-yl)-benzenesulfonyl]-1,2,3,4-tetrahydroisoquinoline (E15) | 480/482 |
| 8-Chloro-7-methoxy-2-[4-methoxy-3-(4-methylpiperazin-1-yl)-benzenesulfonyl]-1,2,3,4-tetrahydroisoquinoline (E16) | 466 |
| 6,7-Dimethoxy-2-[4-methoxy-3-(4-methylpiperazin-1-yl)-benzenesulfonyl]-1,2,3,4-tetrahydroisoquinoline hydrochloride (E17) | 462 |
| 2-[4-Methoxy-3-(4-methylpiperazin-1-yl)-benzenesulfonyl]-7-phenyl-1,2,3,4-tetrahydroisoquinoline hydrochloride (E18) | 478 |
| 8-Bromo-7-methoxy-2-[4-methoxy-3-(4-methylpiperazin-1-yl)-benzenesulfonyl]-1,2,3,4-tetrahydroisoquinoline (E19) | 510/512 |
| 5,6-Dichloro-2-[4-methoxy-3-(4-methylpiperazin-1-yl)-benzenesulfonyl]-1,2,3,4-tetrahydroisoquinoline hydrochloride (E20) | 470/472 |
| 5,8-Dimethoxy-2-[4-methoxy-3-(4-methylpiperazin-1-yl)-benzenesulfonyl]-1,2,3,4-tetrahydroisoquinoline hydrochloride (E21) | 462 |
| 6-Iodo-1-[4-methoxy-3-(4-methylpiperazin-1-yl)benzenesulfonyl]-5-methylthio-2,3-dihydro-1H-indole hydrochloride (E22) | 560 |
| N-(3,4-Dichlorophenyl)-4-methoxy-3-(4-methylpiperazin-1-yl)-benzenesulfonamide hydrochloride (E23) | 430/432 |
| N-(3-Iodophenyl)-4-methoxy-3-(4-methylpiperazin-1-yl)-benzenesulfonamide hydrochloride (E24) | 488 |
| 6,7,8-Trimethoxy-2-[4-methoxy-3-(4-methylpiperazin-1-yl)-benzenesulfonyl]-1,2,3,4-tetrahydroisoquinoline (E25) | 492 |
| 2-[4-Methoxy-3-(4-methylpiperazin-1-yl)-benzenesulfonyl]-6-pyridin-3-yl-2,3-dihydro-1H-indole hydrochloride (E26) | 465 |
| 2-[4-Methoxy-3-(4-methylpiperazin-1-yl)-benzenesulfonyl]-5-pyridin-3-yl-2,3-dihydro-1H-indole hydrochloride (E27) | 465 |

TABLE 2-continued

| Compound | MS (MH+) |
|---|---|
| 1-[4-Methoxy-3-(4-methylpiperazin-1-yl)-benzenesulfonyl]-1,2,3,5-tetrahydropyrrolo[2,3-ƒ]indole hydrochloride (E28) | 427 |
| N-(2-Fluorophenyl)-4-methoxy-3-(4-methylpiperazin-1-yl)benzenesulfonamide hydrochloride (E31) | 380 |
| N-(2-Trifluoromethoxyphenyl)-4-methoxy-3-(4-methyl piperazin-1-yl)-benzenesulfonamide hydrochloride (E32) | 446 |
| N-(2-Bromo-4-methylphenyl)-4-methoxy-3-(4-methylpiperazin-1-yl)-benzenesulfonamide hydrochloride (E33) | 454/456 |
| N-(4-Iodophenyl)-4-methoxy-3-(4-methylpiperazin-1-yl)benzenesulfonamide hydrochloride (E34) | 488 |
| N-(9,10-Dioxo-9,10-dihydroanthracen-1-yl)-4-methoxy-3-(4-methylpiperazin-1-yl)-benzenesulfonamide hydrochloride (E35) | 492 |
| N-(2-Hydroxymethylphenyl)-4-methoxy-3-(4-methylpiperazin-1-yl)-benzenesulfonamide hydrochloride (E36) | 392 |
| 4-Methoxy-3-(4-methylpiperazin-1-yl)-N-(2-methylsulfanylphenyl)-benzenesulfonamide hydrochloride (E37) | 408 |
| 4-Methoxy-3-(4-methylpiperazin-1-yl)-N-(5,6,7,8-tetrahydronaphthalene-1-yl)-benzenesulfonamide hydrochloride (E38) | 416 |
| N-(2-Ethylphenyl)-4-methoxy-3-(4-methylpiperazin-1-yl)benzenesulfonamide hydrochloride (E39) | 390 |
| 4-Methoxy-N-(2-methylphenyl)-3-(4-methylpiperazin-1-yl)benzenesulfonamide hydrochloride (E40) | 376 |
| N-(3,4-Dimethylphenyl)-4-methoxy-3-(4-methylpiperazin-1-yl)-benzenesulfonamide hydrochloride (E41) | 390 |
| 4-Methoxy-N-(2-methoxy-6-methylphenyl)-3-(4-methylpiperazin-1-yl)-benzenesulfonamide hydrochloride (E42) | 406 |
| N-(3-Fluoro-5-pyridin-3-ylphenyl)-4-methoxy-3-(4-methylpiperazin-1-yl)-benzenesulfonamide hydrochloride (E43) | 457 |
| 8-Chloro-2-[4-methoxy-3-(4-methylpiperazin-1-yl)benzenesulfonyl]-1,2,3,4-tetrahydroisoquinoline hydrochloride (E44) | 436/438 |
| N-(2-Chloro-4-fluorophenyl)-4-methoxy-3-(4-methylpiperazin-1-yl)-benzenesulfonamide hydrochloride (E45) | 414/416 |
| N-(2-Trifluorophenyl)-4-methoxy-3-(4-methylpiperazin-1-yl)-benzenesulfonamide hydrochloride (E46) | 430 |
| 4-Methoxy-3-(4-methylpiperazin-1-yl)-N-quinolin-7-ylbenzenesulfonamide hydrochloride (E47) | 413 |
| N-(4-Bromophenyl)-4-methoxy-3-(4-methylpiperazin-1-yl)benzenesulfonamide hydrochloride (E48) | 440/442 |
| N-(3-Bromo-4-methylphenyl)-4-methoxy-3-(4-methylpiperazin-1-yl)-benzenesulfonamide hydrochloride (E49) | 454/456 |
| N-(3-Bromo-2-methylphenyl)-4-methoxy-3-(4-methylpiperazin-1-yl)-benzenesulfonamide hydrochloride (E50) | 454/456 |
| 4-Methoxy-N-(2-methoxydibenzofuran-3-yl)-3-(4-methylpiperazin-1-yl)-benzenesulfonamide hydrochloride (E51) | 482 |
| N-(4-Cyclohexylphenyl)-4-methoxy-3-(4-methylpiperazin-1-yl)-benzenesulfonamide hydrochloride (E52) | 444 |
| N-(2-Iodophenyl)-4-methoxy-3-(4-methylpiperazin-1-yl)benzenesulfonamide hydrochloride (E53) | 488 |
| N-(2-Chloro-4-iodophenyl)-4-methoxy-3-(4-methylpiperazin-1-yl)-benzenesulfonamide hydrochloride (E54) | 522/524 |
| N-(2-Bromo-4-fluorophenyl)-4-methoxy-3-(4-methylpiperazin-1-yl)-benzenesulfonamide hydrochloride (E55) | 458/460 |
| N-[4-(4-Chlorophenyl)thiazol-2-yl]-4-methoxy-3-(4-methylpiperazin-1-yl)-benzenesulfonamide hydrochloride (E56) | 479/481 |
| 4-Methoxy-N-(3-methylphenyl)-3-(4-methylpiperazin-1-yl)benzenesulfonamide hydrochloride (E57) | 376 |
| N-(3-Ethylphenyl)-4-methoxy-3-(4-methylpiperazin-1-yl)benzenesulfonamide hydrochloride (E58) | 390 |
| N-(3-Chloro-4-bromophenyl)-4-methoxy-3-(4-methylpiperazin-1-yl)-benzenesulfonamide hydrochloride (E59) | 474/476 |
| N-(2-Acetylphenyl)-4-methoxy-3-(4-methylpiperazin-1-yl)benzenesulfonamide hydrochloride (E60) | 404 |
| 4-Methoxy-3-(4-methylpiperazin-1-yl)-N-(4-phenylaminophenyl)benzenesulfonamide hydrochloride (E61) | 453 |
| 4-Methoxy-3-(4-methylpiperazin-1-yl)-N-(4-pentyloxyphenyl)benzenesulfonamide hydrochloride (E62) | 448 |
| 4-Methoxy-3-(4-methylpiperazin-1-yl)-N-(4-vinylphenyl)benzenesulfonamide hydrochloride (E63) | 388 |
| 4-Methoxy-3-(4-methylpiperazin-1-yl)-N-(2-pyrrol-1-ylphenyl)-benzenesulfonamide hydrochloride (E64) | 427 |
| 4-Methoxy-3-(4-methylpiperazin-1-yl)-N-[4-(4-nitrophenylsulfanyl)phenyl]-benzenesulfonamide hydrochloride (E65) | 515 |
| 4-Methoxy-3-(4-methylpiperazin-1-yl)-N-(3-oxazol-5-ylphenyl)-benzenesulfonamide hydrochloride (E66) | 429 |
| N-(4-Bromo-3-trifluoromethylphenyl)-4-methoxy-3-(4-methylpiperazin-1-yl)-benzenesulfonamide hydrochloride (E67) | 508/510 |

TABLE 2-continued

| Compound | MS (MH+) |
|---|---|
| 4-Methoxy-N-(2,3-dimethylphenyl)-3-(4-methylpiperazin-1-yl)-benzenesulfonamide hydrochloride (E68) | 390 |
| N-(4-Chloro-3-trifluoromethylphenyl)-4-methoxy-3-(4-methylpiperazin-1-yl)-benzenesulfonamide hydrochloride (E69) | 464/466 |
| 1-[4-Methoxy-3-(4-methylpiperazin-1-yl)benzenesulfonyl]-5-trifluoromethyl-2,3-dihydro-1H-indole hydrochloride (E70) | 456 |
| 7-Bromo-2-[4-methoxy-3-(4-methylpiperazin-1-yl)benzenesulfonyl]-1,2,3,4-tetrahydroisoquinoline hydrochloride (E71) | 480/482 |
| 5,8-Dichloro-2-[4-methoxy-3-(4-methylpiperazin-1-yl)benzenesulfonyl]-1,2,3,4-tetrahydroisoquinoline hydrochloride (E72) | 470/472 |
| 5,7-Dichloro-1-[4-methoxy-3-(4-methylpiperazin-1-yl)benzenesulfonyl]-1,2,3,4-tetrahydroquinoline hydrochloride (E73) | 470/472 |
| 1-[4-Methoxy-3-(4-methylpiperazin-1-yl)benzenesulfonyl]-1,2,3,4-tetrahydroquinoline (E75) | 402 |
| 1-[4-Methoxy-3-(4-methylpiperazin-1-yl)benzenesulfonyl]-6-methyl-1,2,3,4-tetrahydroquinoline (E76) | 416 |
| 6-Fluoro-1-[4-methoxy-3-(4-methylpiperazin-1-yl)benzenesulfonyl]-1,2,3,4-tetrahydroquinoline (E77) | 434 |

EXAMPLE 78

5-Chloro-2-[4-methoxy-3-(4-methylpiperazin-1-yl)-benzenesulphonyl]-2,3-dihydro-1H-isoindole hydrochloride (E78)

Sodium hydride (20 mg of a 60% dispersion in mineral oil, 0.5 mmol) was added to a solution of 3-(4-methyl-1-piperazin-1-yl)-4-methoxybenzenesulphonamide (D16) (53 mg, 0.19 mmol) in DMF (2 ml) in one portion at room temperature under argon. Stirring was continued for 1 hr before a solution of 1,2 bis bromomethyl-4-chlorobenzene (110 mg, 0.37 mmol) in DMF (0.5 ml) was added. The reaction was heated at 60° C. for 3 hrs, cooled and then partitioned between water and dichloromethane. The organic phase was dried over sodium sulphate and concentrated in vacuo. The residue was purified by chromatography on silica gel to afford material which was converted to the title compound by treatment with 1M ethereal HCl. MS: m/z (ME+)=422/424.

EXAMPLE 29

1-(4-Methoxy-3-piperizin-1-ylbenzenesulfonyl)-7-trifluoromethyl-1,2,3,4-tetrahydroquinoline hydrochloride (E29)

A solution of 1-[4-methoxy-3-(4-methylpiperazin-1-yl)benzenesulfonyl]-7-trifluoromethyl-1,2,3,4-tetrahydroquinoline (E8) (70 mg, 0.15 mmol) and 1-chloroethyl chloroformate (0.08 ml, 0.75 mmol) in 1,2-dichloroethane (2 ml) was heated under reflux for 18 h, and then was cooled to ambient temperature. N,N-Diisopropylethylamine (0.05 ml, 0.26 mmol) was added and the resulting solution was heated under reflux for 2 h. The solvent was removed, the residue was dissolved in methanol (4 ml), and the reaction was heated under reflux for 18 h. The solvent was partially removed, dichloromethane (20 ml) was added, and the solution was washed with saturated aqueous sodium hydrogen carbonate (10 ml), dried (MgSO$_4$), and then evaporated. The residue was purified by column chromatography on silica gel eluting with a methanol-dichloromethane gradient to afford the sulfonamide derivative as a yellowish oil. The oil was dissolved in acetone (0.5 ml) and 1M solution of hydrogen chloride in diethyl ether (0.1 ml) was added. The solution was evaporated, and the residue was coevaporated with dry benzene (3×2 ml) to give the title compound (E25) as a cream solid (38 mg, 52%).

$\delta_H$ (250 MHz, DMSO-d$_6$), 1.58 (2H, m), 2.51 (2H, m), 3.01 (4H, br s), 3.16 (4H, br s), 3.79 (2H, t, J=5.80), 3.85 (3H, s), 6.83 (1H, d, J=2.10), 7.13 (1H, d, J=8.74), 7.33 (2H, m), 7.44 (1H, d, J=8.11), 7.95 (1H, s), 9.1 (2H, br s). MS: m/z (MH+)=456.

EXAMPLE 30

N-(3-Bromophenyl)-4-methoxy-3-piperazin-1-ylbenzenesulfonamide (E30)

The title compound was prepared using a similar procedure to that of example E29 using N-(3-bromophenyl)-4-methoxy-3-(4-methylpiperazin-1-yl)benzenesulfonamide (E3) and 1-chloroethyl chloroformate.

$\delta_H$ (250 MHz, DMSO-d$_6$), 2.84 (8H, m), 3.81 (3H, s), 7.01–7.20 (5H, m), 7.23 (1H, m), 7.36 (1H, m). MS: m/z (MH+)=426.

EXAMPLE 79

N-(2-Isopropylphenyl)-4-methoxy-3-piperazin-1-yl-benzenesulfonamide hydrochloride (E79)

Pyridine (0.28 ml) was added to a stirred solution of 2-isopropylaniline (98 mg) and 3-(4-trichloroacetylpiperazin-1-yl)-4-methoxybenzenesulfonyl chloride (D4) (300 mg) in dichloromethane (4 ml) at room temperature. After 18 h the solution was washed with 1M hydrochloric acid (5 ml) then water (5 ml). The organic phase was stirred vigourously with 20% aq. potassium hydroxide (0.5 ml) for 18 h. A 10% aqueous solution of KH$_2$PO$_4$ (8 ml) was then added to the mixture and after 0.25 h stirring the layers were separated. The organic layer was dried (Na$_2$SO$_4$), acidified with 1M ethereal hydrogen chloride (2 ml) and concentrated to an oil which was stirred with acetone/diethyl ether to afford the title compound (E79) as a white solid (0.224 g, 83%). MH+ 390.

The compounds in Table 3 were prepared in a similar manner to Example 79 using 3-(4-trichloroacetylpiperazin-1-yl)-4-methoxybenzenesulfonyl chloride (D4) and the appropriate amine. All amines are either commercially available or can be prepared by methods described above.

TABLE 3

| Compound | MS (MH+) |
|---|---|
| N-(4-Chloronaphthalen-1-yl)-4-methoxy-3-piperazin-1-ylbenzenesulfonamide hydrochloride (E80) | 432/434 |
| 4-Methoxy-N-naphthalen-1-yl-3-piperazin-1-ylbenzenesulfonamide hydrochloride (E81) | 398 |
| N-(3-Chloro-2-methylphenyl)-4-methoxy-3-piperazin-1-ylbenzenesulfonamide hydrochloride (E82) | 396/398 |
| N-Indan-5-yl-4-methoxy-3-piperazin-1-ylbenzenesulfonamide hydrochloride (E83) | 388 |
| N-(2-Fluorophenyl)-4-methoxy-3-piperazin-1-ylbenzenesulfonamide hydrochloride (E84) | 366 |
| 4-Methoxy-N-(2-methylsulfanylphenyl)-3-piperazin-1-ylbenzenesulfonamide hydrochloride (E85) | 394 |
| 4-Methoxy-3-piperazin-1-yl-N-(2-trifluoromethylphenyl)benzenesulfonamide hydrochloride (E86) | 416 |
| 4-Methoxy-N-(2-methylphenyl)-3-piperazin-1-ylbenzenesulfonamide hydrochloride (E87) | 362 |
| N-(2-Ethylphenyl)-4-methoxy-3-piperazin-1-ylbenzenesulfonamide hydrochloride (E88) | 376 |
| 4-Methoxy-3-piperazin-1-yl-N-(3-trifluoromethylphenyl)benzenesulfonamide hydrochloride (E89) | 416 |
| N-(3,4-Dimethylphenyl)-4-methoxy-3-piperazin-1-ylbenzenesulfonamide hydrochloride (E90) | 376 |
| N-(2-Bromophenyl)-4-methoxy-3-piperazin-1-ylbenzenesulfonamide hydrochloride (E91) | 426/428 |
| N-(3,4-Dichlorophenyl)-4-methoxy-3-piperazin-1-ylbenzenesulfonamide hydrochloride E92) | 416/418 |
| N-(3-Iodophenyl)-4-methoxy-3-piperazin-1-ylbenzenesulfonamide hydrochloride (E93) | 474 |
| N-(3,5-Dichlorophenyl)-4-methoxy-3-piperazin-1-ylbenzenesulfonamide hydrochloride (E94) | 416/418 |
| N-(3-Chlorophenyl)-4-methoxy-3-piperazin-1-ylbenzenesulfonamide hydrochloride (E95) | 382/384 |
| N-(2-Chloro-3-fluoro-4-methylphenyl)-4-methoxy-3-piperazin-1-yl-benzenesulfonamide hydrochloride (E96) | 414/416 |
| N-(4-Chloro-3-methylphenyl)-4-methoxy-3-piperazin-l-ylbenzenesulfonamide hydrochloride (E97) | 396/398 |
| N-Benzo[1,3]dioxol-5-yl-4-methoxy-3-piperazin-1-ylbenzenesulfonamide hydrochloride (E98) | 392 |
| N-(2-Bromo-4-methylphenyl)-4-methoxy-3-piperazin-1-ylbenzenesulfonamide hydrochloride (E99) | 440/442 |
| N-(2,5-Dibromophenyl)-4-methoxy-3-piperazin-1-ylbenzenesulfonamide hydrochloride E100) | 504/506 |
| N-(2,5-Dichlorophenyl)-4-methoxy-3-piperazin-1-ylbenzenesulfonamide hydrochloride (E101) | 416/418 |
| N-(2-Chloro-4-methylphenyl)-4-methoxy-3-piperazin-1-ylbenzenesulfonamide hydrochloride (E102) | 396/398 |
| N-(4-Bromophenyl)-4-methoxy-3-piperazin-1-ylbenzenesulfonamide hydrochloride (E103) | 426/428 |
| N-(2-Isopropenylphenyl)-4-methoxy-3-piperazin-1-ylbenzenesulfonamide hydrochloride (E104) | 388 |
| 4-Methoxy-N-(2-methyl-5-nitrophenyl)-3-piperazin-1-ylbenzenesulfonamide hydrochloride (E105) | 407 |
| N-(4-Iodophenyl)-4-methoxy-3-piperazin-1-ylbenzenesulfonamide hydrochloride (E106) | 474 |
| N-(4-tert-Butylphenyl)-4-methoxy-3-piperazin-1-ylbenzenesulfonamide hydrochloride (E107) | 404 |
| N-(4-Isopropylphenyl)-4-methoxy-3-piperazin-1-ylbenzenesulfonamide hydrochloride (E108) | 390 |
| N-(4-Hexylphenyl)-4-methoxy-3-piperazin-1-ylbenzenesulfonamide hydrochloride (E109) | 432 |
| N-(2,4-Dibromonaphthalen-1-yl)-4-methoxy-3-piperazin-1-ylbenzenesulfonamide hydrochloride (E110) | 554/556 |
| 4-Methoxy-N-(4-methoxybiphenyl-3-yl)-3-piperazin-1-ylbenzenesulfonamide hydrochloride (E111) | 454 |
| N-(3-Fluoro-5-pyridin-3-ylphenyl)-4-methoxy-3-piperazin-1-yl-benzenesulfonamide hydrochloride (E112) | 443 |
| N-Biphenyl-2-yl-4-methoxy-3-piperazin-1-ylbenzenesulfonamide hydrochloride (E113) | 424 |
| N-(2-Benzylphenyl)-4-methoxy-3-piperazin-1-ylbenzenesulfonamide hydrochloride (E114) | 438 |
| N-(2-Propylphenyl)-4-methoxy-3-piperazin-1-ylbenzenesulfonamide hydrochloride (E115) | 390 |
| N-(2-sec-Butylphenyl)-4-methoxy-3-piperazin-1-ylbenzenesulfonamide hydrochloride (E116) | 404 |
| N-(2-tert-Butylphenyl)-4-methoxy-3-piperazin-1-ylbenzenesulfonamide hydrochloride (E117) | 404 |

TABLE 3-continued

| Compound | MS (MH+) |
|---|---|
| N-(2-Butylphenyl)-4-methoxy-3-piperazin-1-ylbenzenesulfonamide hydrochloride (E118) | 404 |
| N-(5-Iodo-2-methylphenyl)-4-methoxy-3-piperazin-1-yl-benzenesulfonamide hydrochloride (E119) | 488 |
| N-(2-Chloro-3,5-difluorophenyl)-4-methoxy-3-piperazin-1-ylbenzenesulfonamide hydrochloride (E129) | 418/420 |
| N-(4-Chloro-2-trifluoromethoxyphenyl)-4-methoxy-3-piperazin-1-ylbenzenesulfonamide hydrochloride (E130) | 466/468 |
| N-(2,4,5-Trichlorophenyl)-4-methoxy-3-piperazin-1-ylbenzenesulfonamide hydrochloride (E131) | 450/452 |
| N-(5-Chloro-2-methoxyphenyl)-4-methoxy-3-piperazin-1-ylbenzenesulfonamide hydrochloride (E132) | 412/414 |
| N-(4-Chloro-2-trifluoromethylphenyl)-4-methoxy-3-piperazin-1-ylbenzenesulfonamide hydrochloride (E133) | 450/452 |
| N-(3,5-Dibromophenyl)-4-methoxy-3-piperazin-1-ylbenzenesulfonamide (E134) | 506/508 |
| N-(3-Bromo-2,5-dichlorophenyl)-4-methoxy-3-piperazin-1-ylbenzenesulfonamide hydrochloride (E135) | 494/496 |
| N-(2,3,5-Trichlorophenyl)-4-methoxy-3-piperazin-1-ylbenzenesulfonamide hydrochloride (E136) | 450/452 |
| N-(5-Bromo-2,3-dihydro-benzofuran-7-yl)-4-methoxy-3-piperazin-1-ylbenzenesulfonamide hydrochloride (E137) | 468/470 |
| N-(2-Bromo-3,5-dichlorophenyl)-4-methoxy-3-piperazin-1-ylbenzenesulfonamide (E138) | |
| N-(3-Bromo-5,6-dichlorophenyl)-4-methoxy-3-piperazin-1-ylbenzenesulfonamide (E139) | |
| N-(2,5-Dibromo-3-fluorophenyl)-4-methoxy-3-piperazin-1-ylbenzenesulfonamide (E140) | |
| N-(2,5-Dibromo-3-chlorophenyl)-4-methoxy-3-piperazin-1-ylbenzenesulfonamide (E141) | |
| N-(2,3,5-Tribromophenyl)-4-methoxy-3-piperazin-1-ylbenzenesulfonamide (E142) | |

EXAMPLE 120

6-Chloro-1-(4-methoxy-3-piperazin-1-ylbenzenesulfonyl)-5-methyl-2,3-dihydro-1H-indole hydrochloride (E120)

Pyridine (0.28 ml) was added to a stirred solution of 6-chloro-5-methyl-2,3-dihydro-1H-indole (WO-9501976) (0.116 g) and 3-(4-trichloroacetylpiperazin-1-yl)-4-methoxybenzenesulfonyl chloride (D4) (300 mg) in dichloromethane (4 ml) at room temperature. After 18 h the solution was washed with 1M hydrochloric acid (5 ml), water (5 ml), dried (MgSO$_4$) and concentrated to an oil. The oil was dissolved in 1,4-dioxan (13 ml) and a 0.15 M potassium hydroxide solution (6.5 ml) was added. The solution was stirred at room temperature for 4 h then concentrated to remove the organic solvent, diluted with water (10 ml) and the solution extracted with dichloromethane (20 ml). The organic phase was dried (Na$_2$SO$_4$), acidified with 1M ethereal hydrogen chloride (2 ml), concentrated to a solid and stirred with acetone to afford the title compound (0.175 g, 55%). MH+ 422/424.

The compounds in Table 4 were prepared in a similar manner to Example 120 usin 3-(4-trichloroacetylpiperazin-1-yl)-4-methoxybenzenesulfonyl chloride (D4) and the appropriate amine. All amines are either commercially available or can be prepared by methods described above.

TABLE 4

| Compound | MS (MH+) |
|---|---|
| 6-Iodo-1-(4-methoxy-3-piperazin-1-ylbenzenesulfonyl)-5-methylsulfanyl-2,3-dihydro-1H-indole hydrochloride (E121) | 546 |
| 6-Bromo-1-(4-methoxy-3-piperazin-1-ylbenzenesulfonyl) 1,2,3,4-tetrahydroquinoline hydrochloride (E122) | 466/468 |
| 8-Chloro-2-(4-methoxy-3-piperazin-1-ylbenzenesulfonyl)-1,2,3,4-tetrahydroisoquinoline hydrochloride (E123) | 422/424 |
| 1-(4-Methoxy-3-piperazin-1-ylbenzenesulfonyl)-5-methyl-6-trifluoromethyl-2,3-dihydro-1H-indole hydrochloride (E124) | 456 |
| 6-Iodo-1-(4-methoxy-3-piperazin-1-ylbenzenesulfonyl)-2,3-dihydro-1H-indole hydrochloride (E143) | 500 |
| 5-Iodo-1-(4-methoxy-3-piperazin-1-ylbenzenesulfonyl)-2,3-dihydro-1H-indole hydrochloride (E144) | 500 |
| 7-Bromo-1-(4-methoxy-3-piperazin-1-ylbenzenesulfonyl)-1,2,3,4-tetrahydroquinoline hydrochloride (E145) | 466/468 |

EXAMPLE 125

5,8-Dimethoxy-2-(4-methoxy-3-piperazin-1-ylbenzensulfonyl)-1,2,3,4-tetrahydroisoquinoline hydrochloride (E125)

A solution of 1-chloroethylchloroformate (0.12 ml;1.11 mmol) and 5,8-dimethoxy-2-[4-methoxy-3-(4-methyl-1-piperazinyl)benzenesulfonyl]-1,2,3,4-tetrahydroisoquinoline (E21) (111 mg;0.223 mmol) in 1,2-dichloroethane (3 ml) was refluxed for 0.75 h, cooled, diluted with diisopropylethylamine (0.19 ml;1.11 mmol) and refluxed for a further 2.5 hrs. The solution was concentrated to a residue which was re-dissolved in methanol, refluxed for 1 hr and then stirred at room temperature for 24 h. The mixture was concentrated, and the residue partitioned between ethyl acetate and aqueous sodium bicarbonate solution. The organic layer was dried, concentrated to a residue and purified by column chromatography on silica gel using a methanol/dichloromethane solvent gradient. The title compound was prepared by dissolving the pure free base material from chromatography in acetone/dichloromethane and acidifying with 1M ethereal HCl (53 mg, 49%). MH+456/458.

EXAMPLE 126

5,8-Dichloro-2-(4-methoxy-3-piperazin-1-ylbenzenesulfonyl)-1,2,3,4-tetrahydroisoquinoline hydrochloride (E126)

The title compound was prepared from its N-methylpiperazine analogue (E72) by a method as described in E125, but the reaction was kept at ambient temperature and the diisopropylethylamine was added at the start of the reaction. MH+ 456/458.

EXAMPLE 127

N-(3-Iodo-4-methylphenyl)-4-methoxy-3-piperazin-1-yl-benzenesulfonamide hydrochloride (E127)

The title compound was prepared from its N-methylpiperazine analogue (E9) by a method as described in E125. MH+ 488.

EXAMPLE 128

5,7-Dichloro-1-(4-methoxy-3-piperazin-1-ylbenzenesulfonyl)-1,2,3,4-tetrahydroquinoline hydrochloride (E128)

The title compound was prepared from its N-methylpiperazine analogue (E73) by a method as described in E125. MH+ 456/458.

Pharmacological Data
Method for Assay of 5-HT6 Antagonistic Activity

The test compounds were dissolved in polyethylene glycol:dimethyl sulphoxide (1:1) at 1 or 10 mM and diluted to 0.1 mM using 5 mM tris buffer (pH 7.7 @ 25° C.). Dissolution was assisted by addition of 0.02 ml 5M HCl plus heating to 40° C. and sonication for 10 minutes. Serial dilutions of drugs in the same buffer were carried out using either a TECAN 5052 or Biomek 2000 Workstation. Samples of the diluted test compounds (0.05 ml) were mixed with 0.05 ml of radio-ligand [$^3$H]-LSD prepared in the incubation buffer, and 0.4 ml of a suspension of a preparation of the washed membranes of HeLa_5HT6 cells (acquired from Dr. D. Sibley, NIH, Bethesda, see Ref 1)(see Table 1), also in the incubation buffer. The details of the incubation conditions for each assay are shown in Table 2. The incubation buffer was 50 mM Trizma (Sigma, UK) pH7.7 @ 25° C., 4 mM $MgCl_2$.

After incubation at 37° C., the mixtures were filtered using a Packard Filtermate in Packard TopCount format. Filters were washed with 4×1 ml aliquots of ice-cold incubation buffer. Filters were dried and impregnated with 0.04 ml of Microscint 20 (Packard). $IC_{50}$ values were estimated from the counts per minute using a four parameter logistic curve fit within EXCEL (2). $K_i$ values were calculated using the method of Cheng and Prusoff(3). $pIC_{50}$ and $pK_i$ are the negative log10 of the molar $IC_{50}$ and $K_i$ respectively.

TABLE 1

Details of the methods used to prepare membranes for binding assays

| 1st resuspension cells/ml | spin/resuspension 1,2,3 | Incubation before final spin | protein conc. in stored aliquots | cells/ml in stored aliquots |
|---|---|---|---|---|
| $7 \times 10^7$ | Yes | 20 min at 37° C. | 4 mg/ml | $1.0 \times 10^8$ |

TABLE 2

Summary of receptor binding assay conditions

| protein (ug/sample) | radio-ligand [$^3$H]-LSD (nM) | Specific Activity (Ci/mmol) | Non-Specific Definition | kD (nM) |
|---|---|---|---|---|
| 40 | 2.0 | 83 | Methiothepin | 3.1 |

REFERENCES

1. MONSMA, F. J., SHEN, Y., WARD, R. P., HAMBLIN, M. W., SIBLEY, D. R. 1993. Cloning and expression of a novel serotonin receptor with high affinity for tricyclic psychotropic drugs. *Mol. Pharmacol.*, 43, 320–327.
2. BOWEN, W. P., JERMAN, J. C. 1995. Nonlinear regression using spreadsheets. *Trends in Pharmacol. Sci.*, 16, 413–417.
3. CHENG, Y. C., PRUSSOF, W. H. 1973. Relationship between inhibition constant (Ki) and the concentration of inhibitor which causes 50% inhibition (IC50) of an enzymatic reaction. *Biochem. Pharmacol.*, 92, 881–894.

All compounds tested showed good selective 5-HT6 receptor antagonist activity, having pKi values 7.5–9.5 at human cloned 5-HT6 receptors. Particularly preferred compounds demonstrated pKi>8.5 and selectivity>100. Examples of such compounds include: 3, 8, 21, 29, 32, 37–39, 41, 44, 45, 53, 54, 57–59, 63, 67, 69, 72, 73, 79, 85, 88, 89, 91,93–95, 100, 104, 107, 113, 117–119, 121–128, 131, 132, 134–143, 145.

What is claimed is:

1. A compound of formula (I) or a salt thereof:

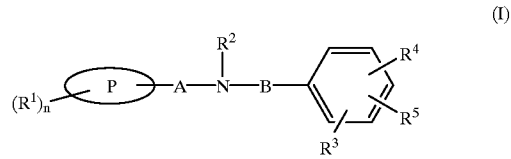

(I)

wherein:
P is phenyl, or naphthyl;
A is a single bond, a $C_{1-6}$alkylene or a $C_{1-6}$alkenylene group;

B is SO$_2$;

R$^1$ is halogen, C$_{1-6}$alkyl optionally substituted by one or more fluorine atoms, C$_{3-6}$cycloalkyl, C$_{2-6}$alkenyl, C$_{2-6}$alkynyl, C$_{1-6}$alkanoyl, C$_{1-6}$alkoxy, OCF$_3$, hydroxy, hydroxyC$_{1-6}$alkyl, hydroxyC$_{1-6}$alkoxy, C$_{1-6}$alkoxyC$_{1-6}$alkoxy, nitro, cyano, NR$^{10}$R$^{11}$ where R$^{10}$ and R$^{11}$ are independently hydrogen, C$_{1-6}$alkyl or optionally substituted phenyl, SR$^{11}$ where R$^{11}$ is as defined above or R$^1$ is optionally substituted phenyl, naphthyl, a bicyclic heterocyclic ring or is a 5 to 7-membered heterocyclic ring each containing 1 to 4 heteroatoms selected from oxygen, nitrogen or sulphur, or R$^1$ together with a second R$^1$ substituent forms a group —O—CH$_2$—O—, OCH$_2$CH$_2$O—, —CH$_2$CH$_2$CH$_2$— or —CH$_2$CH$_2$CH$_2$CH$_2$—, n is 0, 1, 2, 3, 4, 5 or 6;

R$^2$ is hydrogen, C$_{1-6}$ alkyl, aryl C$_{1-6}$ alkyl or together with group P form a 5 to 8 membered ring optionally substituted with one or more C$_{1-6}$alkyl groups;

R$^3$ is hydrogen, halogen, C$_{1-6}$alkyl, C$_{3-6}$cycloalkyl, C$_{1-6}$alkanoyl, C$_{1-6}$alkoxy optionally substituted with one or more fluorine atoms, hydroxy, hydroxyC$_{1-6}$alkyl, hydroxyC$_{1-6}$alkoxy, C$_{1-6}$alkoxyC$_{1-6}$alkoxy, nitro, trifluoromethyl, cyano or aryl or together with the group R$^5$ forms a group (CH$_2$)$_2$O or (CH$_2$)$_3$O optionally substituted with 1 or more C$_{1-6}$alkyl groups;

R$^4$ is piperazine, optionally substituted by C1-6alkyl with a meta relationship with the group B; and R$^5$ is methoxy with a para relationship to the group B.

2. A compound according to claim 1 in which R$^1$ is hydrogen, halogen, C$_{1-6}$alkoxy or C$_{1-6}$alkyl optionally substituted by one or more halogen atoms.

3. A compound according to claim 2 in which R$^5$ is methoxy.

4. A compound according to claim 1 which is:

N-(3-Bromophenyl)-4-methoxy-3-(4-methylpiperazin-1-yl)benzene sulfonamide,
1-[4-Methoxy-3-(4-methylpiperazin-1-yl)-benzenesulfonyl]-7-trifluoromethyl-1,2,3,4-tetrahydroquinoline,
5,8-Dimethoxy-2-[4-methoxy-3-(4-methylpiperazin-1-yl)-benzenesulfonyl]-1,2,3,4-tetrahydroisoquinoline,
1-(4-Methoxy-3-piperazin-1-ylbenzenesulfonyl)-7-trifluoromethyl-1,2,3,4-tetrahydroquinoline,
N-(2-Trifluoromethoxyphenyl)-4-methoxy-3-(4-methylpiperazin-1-yl)-benzenesulfonamide,
4-Methoxy-3-(4-methylpiperazin-1-yl)-N-(2-methylsulfanylphenyl)-benzenesulfonamide,
4-Methoxy-3-(4-methylpiperazin-1-yl)-N-(5,6,7,8-tetrahydronaphthalene-1-yl)-benzenesulfonamide,
N-(2-Ethylphenyl)-4-methoxy-3-(4-methylpiperazin-1-yl)benzenesulfonamide,
N-(3,4-Dimethylphenyl)-4-methoxy-3-(4-methylpiperazin-1-yl)-benzenesulfonamide,
8-Chloro-2-[4-methoxy-3-(4-methylpiperazin-1-yl)benzenesulfonyl]-1,2,3,4-tetrahydroisoquinoline,
N-(2-Chloro-4-fluorophenyl)-4-methoxy-3-(4-methylpiperazin-1-yl)-benzenesulfonamide,
N-(2-Iodophenyl)-4-methoxy-3-(4-methylpiperazin-1-yl)benzenesulfonamide,
N-(2-Chloro-4-iodophenyl)-4-methoxy-3-(4-methylpiperazin-1-yl)-benzenesulfonamide,
4-Methoxy-N-(3-methylphenyl)-3-(4-methylpiperazin-1-yl)benzenesulfonamide,
N-(3-Ethylphenyl)-4-methoxy-3-(4-methylpiperazin-1-yl)benzenesulfonamide,
N-(3-Chloro-4-bromophenyl)-4-methoxy-3-(4-methylpiperazin-1-yl)-benzenesulfonamide,
4-Methoxy-3-(4-methylpiperazin-1-yl)-N-(4-vinylphenyl)benzenesulfonamide,
N-(4-Bromo-3-trifluoromethylphenyl)-4-methoxy-3-(4-methylpiperazin-1-yl)-benzenesulfonamide,
N-(4-Chloro-3-trifluoromethylphenyl)-4-methoxy-3-(4-methylpiperazin-1-yl)-benzenesulfonamide,
5,8-Dichloro-2-[4-methoxy-3-(4-methylpiperazin-1-yl)benzenesulfonyl]-1,2,3,4-tetrahydroisoquinoline,
5,7-Dichloro-1-[4-methoxy-3-(4-methylpiperazin-1-yl)benzenesulfonyl]-1,2,3,4-tetrahydroquinoline,
N-(2-Isopropylphenyl)-4-methoxy-3-piperazin-1-ylbenzenesulfonamide hydrochloride,
4-Methoxy-N-(2-methylsulfanylphenyl)-3-piperazin-1-ylbenzenesulfonamide,
N-(2-Ethylphenyl)-4-methoxy-3-piperazin-1-ylbenzenesulfonamide,
4-Methoxy-3-piperazin-1-yl-N-(3-trifluoromethylphenyl)benzenesulfonamide,
N-(2-Bromophenyl)-4-methoxy-3-piperazin-1-ylbenzenesulfonamide,
N-(3-Iodophenyl)-4-methoxy-3-piperazin-1-ylbenzenesulfonamide,
N-(3,5-Dichlorophenyl)-4-methoxy-3-piperazin-1-ylbenzenesulfonamide,
N-(3-Chlorophenyl)-4-methoxy-3-piperazin-1-ylbenzenesulfonamide,
N-(2,5-Dibromophenyl)-4-methoxy-3-piperazin-1-ylbenzenesulfonamide,
N-(2-Isopropenylphenyl)-4-methoxy-3-piperazin-1-ylbenzenesulfonamide,
N-(4-tert-Butylphenyl)-4-methoxy-3-piperazin-1-ylbenzenesulfonamide,
N-Biphenyl-2-yl-4-methoxy-3-piperazin-1-ylbenzenesulfonamide,
N-(2-tert-Butylphenyl)-4-methoxy-3-piperazin-1-ylbenzenesulfonamide,
N-(2-Butylphenyl)-4-methoxy-3-piperazin-1-ylbenzenesulfonamide,
N-(5-Iodo-2-methylphenyl)-4-methoxy-3-piperazin-1-ylbenzenesulfonamide,
6-Iodo-1-(4-methoxy-3-piperazin-1-ylbenzenesulfonyl)-5-methylsulfanyl-2,3-dihydro-1H-indole,
6-Bromo-1-(4-methoxy-3-piperazin-1-ylbenzenesulfonyl)-1,2,3,4-tetrahydroquinoline,
8-Chloro-2-(4-methoxy-3-piperazin-1-ylbenzenesulfonyl)-1,2,3,4-tetrahydroisoquinoline,
1-(4-Methoxy-3-piperazin-1-ylbenzenesulfonyl)-5-methyl-6-trifluoromethyl-2,3-dihydro-1H-indole,
5,8-Dimethoxy-2-(4-methoxy-3-piperazin-1-ylbenzensulfonyl)-1,2,3,4-tetrahydroisoquinoline hydrochloride,
5,8-Dichloro-2-(4-methoxy-3-piperazin-1-ylbenzenesulfonyl)-1,2,3,4-tetrahydroisoquinoline hydrochloride,
N-(3-Iodo-4-methylphenyl)-4-methoxy-3-piperazin-1-ylbenzenesulfonamide,
5,7-Dichloro-1-(4-methoxy-3-piperazin-1-ylbenzenesulfonyl)-1,2,3,4-tetrahydroquinoline,
N-(2,4,5-Trichlorophenyl)-4-methoxy-3-piperazin-1-ylbenzenesulfonamide,
N-(5-Chloro-2-methoxyphenyl)-4-methoxy-3-piperazin-1-ylbenzenesulfonamide,
N-(3,5-Dibromophenyl)-4-methoxy-3-piperazin-1-ylbenzenesulfonamide,
N-(3-Bromo-2,5-dichlorophenyl)-4-methoxy-3-piperazin-1-ylbenzenesulfonamide, N-(2,3,5-Trichlorophenyl)-4-methoxy-3-piperazin-1-ylbenzenesulfonamide,
N-(5-Bromo-2,3-dihydro-benzofuran-7-yl)-4-methoxy-3-piperazin-1-ylbenzenesulfonamide,
N-(2-Bromo-3,5-dichlorophenyl)-4-methoxy-3-piperazin-1-ylbenzenesulfonamide,
N-(3-Bromo-5,6-dichlorophenyl)-4-methoxy-3-piperazin-1-ylbenzenesulfonamide,
N-(2,5-Dibromo-3-fluorophenyl)-4-methoxy-3-piperazin-1-ylbenzenesulfonamide,
N-(2,5-Dibromo-3-chlorophenyl)-4-methoxy-3-piperazin-1-ylbenzenesulfonamide,
N-(2,3,5-Tribromophenyl)-4-methoxy-3-piperazin-1-ylbenzenesulfonamide,
6-Iodo-1-(4-methoxy-3-piperazin-1-ylbenzenesulfonyl)-2,3-dihydro-1H-indole, and
7-Bromo-1-(4-methoxy-3-piperazin-1-ylbenzenesulfonyl)-1,2,3,4-tetrahydroquinoline and pharmaceutically acceptable salts thereof.

5. A pharmaceutical composition which comprises a compound according to claim 1 and a pharmaceutically acceptable carrier or excipient.

6. A process for the preparation of a compound of formula (I) or a pharmaceutically acceptable salt thereof, which process comprises the coupling of a compound of formula (II):

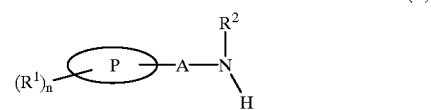

in which $R^1$, $R^2$, n, P, and A are as defined in formula (I) or protected derivatives thereof with a compound of formula (III):

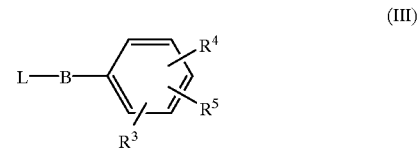

in which B, $R^3$, $R^4$ and $R^5$ are as defined in formula (I) or protected derivatives thereof and L is a leaving group and optionally thereafter
removing any protecting groups
forming a pharmaceutically acceptable salt.

7. A method of treating anxiety and/or depression comprising administering to a subject a safe and effective amount of a compound according to claim 1.

* * * * *